US012685832B2

(12) United States Patent
Gutierrez et al.

(10) Patent No.: US 12,685,832 B2
(45) Date of Patent: Jul. 21, 2026

(54) DEVICE FOR FACILITATING RESPIRATORY MONITORING AND SUPPORT FOR PATIENTS

(71) Applicant: University of Virginia Patent Foundation, Charlottesville, VA (US)

(72) Inventors: Claudia N. Gutierrez, Charlottesville, VA (US); Rachel Hollingsworth Jonas, Charlottesville, VA (US); Samuel Oyer, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 19/196,695

(22) Filed: May 1, 2025

(65) Prior Publication Data

US 2025/0339636 A1 Nov. 6, 2025

Related U.S. Application Data

(60) Provisional application No. 63/642,413, filed on May 3, 2024, provisional application No. 63/641,191, filed on May 1, 2024.

(51) Int. Cl.
*A61M 16/04* (2006.01)
*A61B 5/083* (2006.01)

(52) U.S. Cl.
CPC ......... *A61M 16/049* (2014.02); *A61B 5/0836* (2013.01)

(58) Field of Classification Search
CPC ........... A61M 16/049; A61M 16/0493; A61M 16/0495; A61M 16/0497; A61M 16/0488
See application file for complete search history.

(56) References Cited

U.S. PATENT DOCUMENTS 4,877,024 A * 10/1989 Sheehy ............. A61M 16/0493
128/207.14
8,443,797 B2 * 5/2013 Hauge ............... A61M 16/0497
128/207.14

(Continued)

*Primary Examiner* — Colin W Stuart
*Assistant Examiner* — Douglas Y Sul
(74) *Attorney, Agent, or Firm* — Thomas I Horstemeyer, LLP

(57) ABSTRACT

The Respiratory Interface Device is a novel, mouth-inserted airway management tool designed to facilitate both oxygen delivery and carbon dioxide sampling through an integrated oral pathway. Unlike conventional nasal cannulas or oropharyngeal airways, this device features internal channels configured to house standard or capnography-compatible tubing, allowing simultaneous gas delivery and exhaled gas monitoring. The device includes a contoured dental plate and an airway arch that conforms to the patient's hard palate, maintaining upper airway patency while avoiding stimulation of the protective airway reflex. Its ergonomic design supports a secure oral fit and provides a streamlined interface for procedural sedation, monitored anesthesia care, emergency airway support, and alternative oxygenation strategies in patients where nasal access is limited or contraindicated. The Respiratory Interface Device represents a versatile, dual-function solution for enhanced airway management and respiratory monitoring.

17 Claims, 10 Drawing Sheets

(56) References Cited

U.S. PATENT DOCUMENTS

| | | | |
|---|---|---|---|
| 11,744,970 B2* | 9/2023 | Birch ................ | A61M 16/0486 |
| | | | 128/207.14 |
| 2004/0129272 A1* | 7/2004 | Ganesh ............ | A61M 16/0495 |
| | | | 128/207.14 |
| 2006/0272647 A1* | 12/2006 | Hauge ............... | A61M 16/0493 |
| | | | 128/207.14 |
| 2021/0162156 A1* | 6/2021 | Farrell ................ | A61M 16/049 |
| 2022/0249791 A1* | 8/2022 | Parker ................ | A61B 1/00154 |
| 2024/0075232 A1* | 3/2024 | Peterson ........... | A61M 16/0495 |
| 2025/0121152 A1* | 4/2025 | Picha, III ......... | A61M 16/0672 |

* cited by examiner

100

224

222

DEVICE FOR FACILITATING RESPIRATORY MONITORING AND SUPPORT FOR PATIENTS

CROSS-REFERENCE TO RELATED APPLICATIONS

This application claims the benefit of U.S. Provisional Patent Application Ser. No. 63/641,191, filed May 1, 2024 and U.S. Provisional Patent Application Ser. No. 63/642, 413, filed May 3, 2024, the disclosures of which are hereby incorporated herein by reference in their entirety.

BACKGROUND

During certain medical procedures, the ability to deliver oxygen and monitor carbon dioxide as a surrogate for respiration may be required. Oxygen (O2) delivery and carbon dioxide (CO2) monitoring via the nose can be difficult or problematic, during particular types of procedures or in the setting of nasal pathology. Accordingly, there is a need for devices that allow for the delivery of oxygen and monitoring of carbon dioxide during medical procedures.

SUMMARY

In accordance with the purpose(s) of the present disclosure, as embodied and broadly described herein, the disclosure, in one aspect, relates to a Respiratory Interface Device, system and related methods thereof. Various embodiments can include a respiratory interface device, system, and related methods that enable oxygen delivery and/or carbon dioxide monitoring during various medical procedures as desired or required.

A respiratory interface device, in various embodiments, comprises: (1) a dental plate defining at least one conduit receiving cutout; (2) a bridge portion extending rearward from the dental plate; and (3) a substantially elliptical quadrant shaped airway arch arcing from the bridge portion from an opposing portion of the bridge portion from the dental plate, the airway arch defining an air outlet on a back face of the airway arch, wherein the respiratory interface device defines at least one channel that extends from the at least one conduit receiving cutout, through the bridge portion and the airway arch, and terminating at the air outlet.

In some embodiments, the at least one channel is configured to receive at least one conduit through the at least one conduit receiving cutout and maintain an end of the at least one conduit adjacent the air outlet. In various embodiments, the at least one channel is at least partially enclosed. In some embodiments, the air outlet is disposed at a height greater than the at least one conduit receiving cutout when the respiratory interface device is in a neutral position with the bridge portion parallel to the ground.

In particular embodiments, the airway arch is configured to engage a hard palate of a patient when inserted into a mouth of the patient without triggering a protective airway reflex of the patient. In some embodiments, the dental plate is configured to at least partially engage at least a portion of one or more lips or teeth of the patient to maintain the respiratory interface device at a desired distance into the mouth of the patient. In particular embodiments, the respiratory interface device comprises at least one of thermoplastic polyurethane or thermoplastic elastomer.

A respiratory interface device for a patient, in some embodiments, comprises: (1) a dental plate defining a front face and a rear face; (2) a bridge portion extending rearward from the rear face of the dental plate; and (3) an airway arch arcing from the bridge portion from an opposing portion of the bridge portion from the dental plate, wherein the oral device defines at least one channel that extends from the front face of the dental plate through the bridge portion and the airway arch and terminates at a rear portion of the airway arch. In various embodiments, the airway arch is configured such that the rear portion of the airway arch is disposed substantially adjacent a mark that is substantially ⅔rds back on a hard palate of the patient when the oral device is placed in a mouth of the patient. In some embodiments, an end of the at least one channel is disposed substantially adjacent the mark that is substantially ⅔rds back on the hard palate of the patient when the oral device is placed in the mouth of the patient.

In particular embodiments, the at least one channel comprises a first channel and a second channel and each of the first channel and the second channel are each configured to respectively receive and at least temporarily maintain at least a portion of at least one conduit, the at least one conduit comprising a first tubing for oxygen delivery and a second tubing for carbon dioxide sampling. In some embodiments, the airway arch has a shape that is a substantially elliptical quadrant. In particular embodiments, the airway arch is configured to engage at least a portion of the hard palate of the patient when the oral device is placed in the mouth of the patient.

In particular embodiments, the airway arch is configured to extend into the mouth of the patient sufficiently far to provide oxygen through at least one channel in a desired position within the mouth without triggering a protective airway reflex of the patient. In some embodiments, the at least one channel is configured to provide oxygen delivery to the mouth of the patient and a return flow of carbon dioxide from the mouth of the patient. In various embodiments, the oral device may comprise a variety of biocompatible materials including, but not limited to, silicone, thermoplastic elastomers (TPE), polyurethane, or medical-grade rubber. The selected material may vary depending on the desired rigidity, flexibility, or transparency of the device. In particular embodiments, the dental plate comprises an upper lip engaging portion that extends upward from a distal portion of the dental plate and a lower lip engaging portion that extends downward from the distal portion of the dental plate; and the dental plate is substantially c-shaped.

In particular embodiments, the dental plate has a height that is about 1.5 times a height of the bridge portion. In various embodiments, the oral device is sufficiently rigid such that a biting force from the patient when the oral device is in the mouth of the patient does not deform the at least one channel.

A method of delivering oxygen to a patient or monitoring carbon dioxide from a patient during a medical procedure, in various embodiments, comprises: (1) providing a respiratory interface device comprising: (A) a dental plate defining a front face, a rear face, and an oxygen inlet; (B) an airway arch arcing from the rear face of the dental plate and defining an oxygen outlet, wherein the respiratory interface device defines at least one channel that extends from the oxygen inlet to the oxygen outlet through at least a portion of the airway arch. In some embodiments, the airway arch is configured such that the oxygen outlet is disposed substantially adjacent a mark that is substantially ⅔rds back on a hard palate of the patient when the respiratory interface device is placed in a mouth of the patient. In various embodiments, the method further comprises: (1) inserting the respiratory interface device into the mouth of the patient such that the dental place is adjacent a front of the mouth of the patient, and the airway arch extends about two-thirds back of the hard palate of the patient; and (2) causing at least one of: (A) oxygen to flow through the at least one channel and exit the at least one channel adjacent the oxygen outlet; or (B) detection of carbon dioxide exhaled by the patient through the at least one channel.

In various embodiments, inserting at least one tubing through the oxygen inlet and the at least one channel until an end of the at least one tubing is adjacent the oxygen outlet; and causing the oxygen to flow through the at least one tubing. In still other embodiments, the method further comprises inserting the respiratory interface device into the mouth of the patient without triggering a protective airway reflex of the patient.

Other systems, methods, features, and advantages of the present disclosure will be or become apparent to one with skill in the art upon examination of the following drawings and detailed description. It is intended that all such additional systems, methods, features, and advantages be included within this description and be within the scope of the present disclosure. In addition, all optional and preferred features and modifications of the described embodiments are usable in all aspects of the disclosure taught herein.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Drawings are presented in the attachment files accompanying this specification.

DETAILED DESCRIPTION

Figure 1:
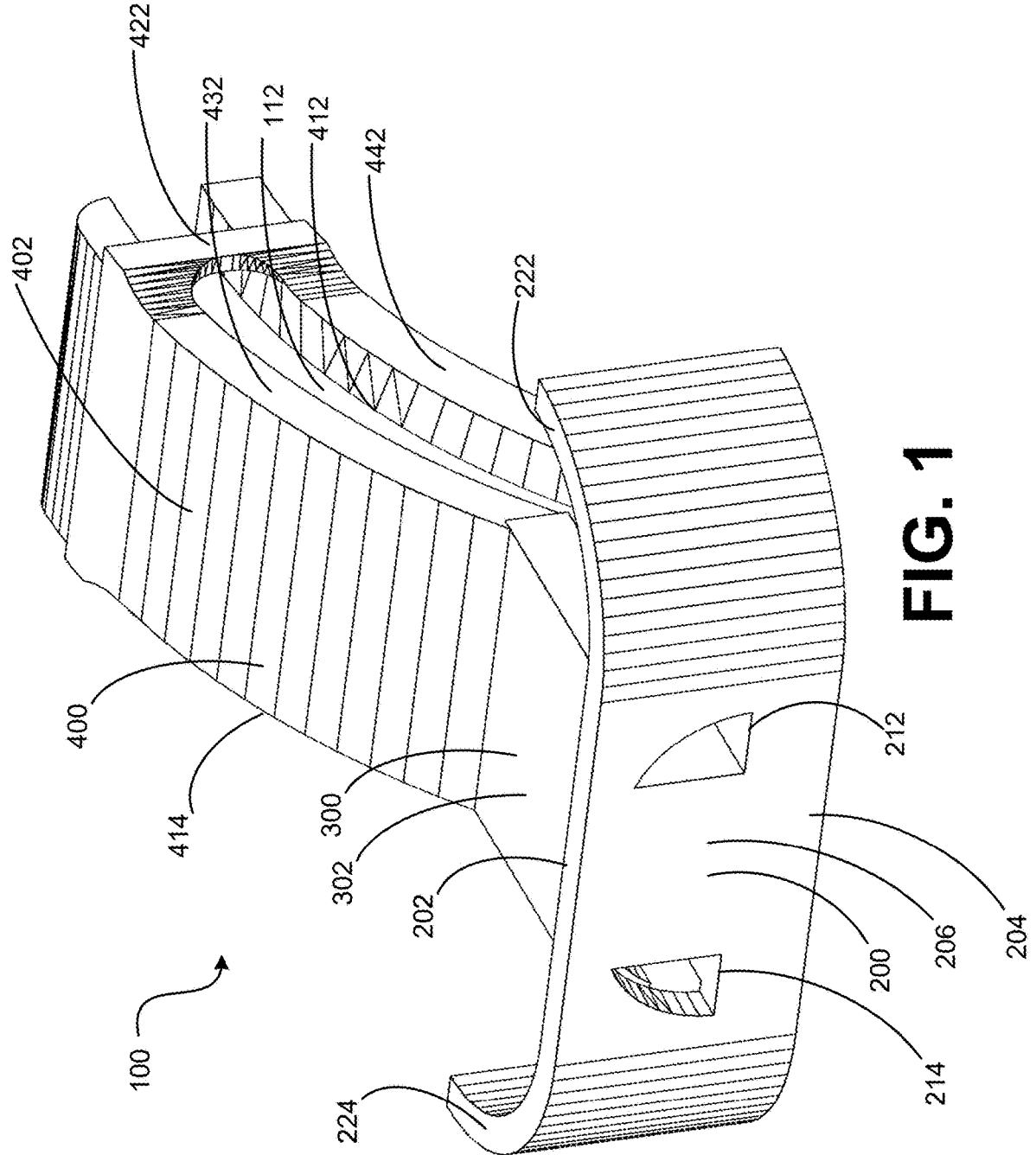
FIG. 1 is a perspective view of a respiratory interface device in accordance with various embodiments of the present disclosure.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the disclosure. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method and/or process can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by," "comprising," "comprises," "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an," and "the" include plural referents unless the context clearly dictates otherwise. Thus, for example, reference to "a spacer," "a guide nucleic acid," or "an miRNA," including, but not limited to, mixtures or combinations of two or more such spacers, guide nucleic acids, or miRNAs, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

Overview

As noted above, there is a need for improved devices and techniques for oxygen delivery during medical procedures. In addition, there is a need for improved devices and techniques to detect exhaled carbon dioxide during such procedures. In particular, in the context of medical procedures where patients have varying levels of consciousness, whether or be secondary to intoxication or the use of sedating medications, there may be difficulties in providing consistent, sufficient oxygen in a manner that does not interfere with the procedure. Additionally, in the context of patients that require oxygen delivery and carbon dioxide detection to confirm gas exchange in the lungs, some patients may not require any level of sedation or anesthesia. For example, because patients are generally conscious during monitored anesthesia care and are conscious in situations in which the patients are not sedated at all, the use of an oropharyngeal airway may not be appropriate for these patients due to these patients presenting with protective airway reflexes (e.g., gag/pharyngeal reflect, cough reflex, or laryngospasm).

Oxygen delivery and/or carbon dioxide monitoring can be particularly difficult during facial surgeries. For example, the use of a nasal cannula may not be possible as, due to the placement location of a nasal cannula, the nasal cannula may interfere with the procedure e.g. reconstruction of the nostril after a skin cancer removal. Surgeons may place a traditional nasal cannula into the patient's mouth during such procedures. Such a technique, however, may not provide the required oxygen delivery as the patient may move their lips, teeth, or tongue in a manner that blocks or otherwise restricts the airflow. Resolving such obstructions during a procedure can require manual interventions from surgeons, which can break the sterile field, distract from the procedure itself, or prolong the length of surgery.

In yet another example, a patient may have a broken nose and be unable to receive oxygen via a nasal cannula. Such patients may not require sedation, so techniques may be required that enable oxygen delivery and/or gas exchange confirmation. Various embodiments described herein may provide an oral respiratory interface device that does not trigger a patient's protective airway reflex (e.g., because the oral respiratory interface device does not extend far enough into the patient's mouth to trigger such a reflex).

FIG. 1 depicts a respiratory interface device 100 in accordance with various embodiments of the present disclosure. In some embodiments, the respiratory interface device 100 comprises a respiratory interface device that is configured to facilitate delivery of oxygen to a patient. Although the device 100 shown in FIG. 1 is, in some embodiments, referred to as a respiratory interface device 100, it should be understood that, in other embodiments, the device may provide other functionality in addition to oxygen delivery. For example, in particular embodiments, the device 100 is configured to provide one or more pathways for the return of carbon dioxide exhaled by a patient in whose mouth the device 100 has been placed. In this way, the device is configured to provide oxygen to the patient and enable detection of exhaled carbon dioxide. As such, the device 100, in particular embodiments, is configured to enable confirmation of gas exchange in a patient's lungs while the device is inserted into the patient's mouth and being used to deliver oxygen and facilitate the detection of exhaled carbon dioxide. In some embodiments, the respiratory interface device 100 comprises an oral respiratory interface device that is configured for insertion in a patient's mouth. In other embodiments, the respiratory interface device 100 may be configured for placement on or near any other suitable portion of a patient.

As may be understood in light of this disclosure, the respiratory interface device 100 is configured to house tubing that delivers oxygen and/or tubing that allows for the outflow of carbon dioxide. In some embodiments, the device 100 is configured to at least temporarily house one or more conduits in order to maintain each of the one or more conduits in a position and orientation that protects the one or more conduits from obstructions during surgical procedures. In particular, the respiratory interface device 100 is configured to at least temporarily receive the one or more conduits, and maintain them in a position to provide sufficient, consistent oxygen delivery. In still other embodiments, the respiratory interface device 100 is configured to receive any other suitable number of conduits in order to deliver oxygen and allow for the return of carbon dioxide through the device. In some embodiments, the one or more conduits may include any suitable tubing, any suitable nasal cannula or portion thereof, etc. In some embodiments, the conduit and/or tubing includes the tubing from an End-Tidal Co2 nasal cannula, which has one tubing for oxygen delivery and another for CO2 sampling by taking a first and second nasal cannula tube (e.g., by cutting the tubes from a traditional End-tidal Co2 nasal cannula).

As may be understood from FIG. 1, the respiratory interface device 100 comprises a dental plate 200 adjacent a front portion of the respiratory interface device 100, a bridge portion 300 adjacent the dental plate 200, and an airway arch 400 adjacent the bridge portion 300.

Figure 8:
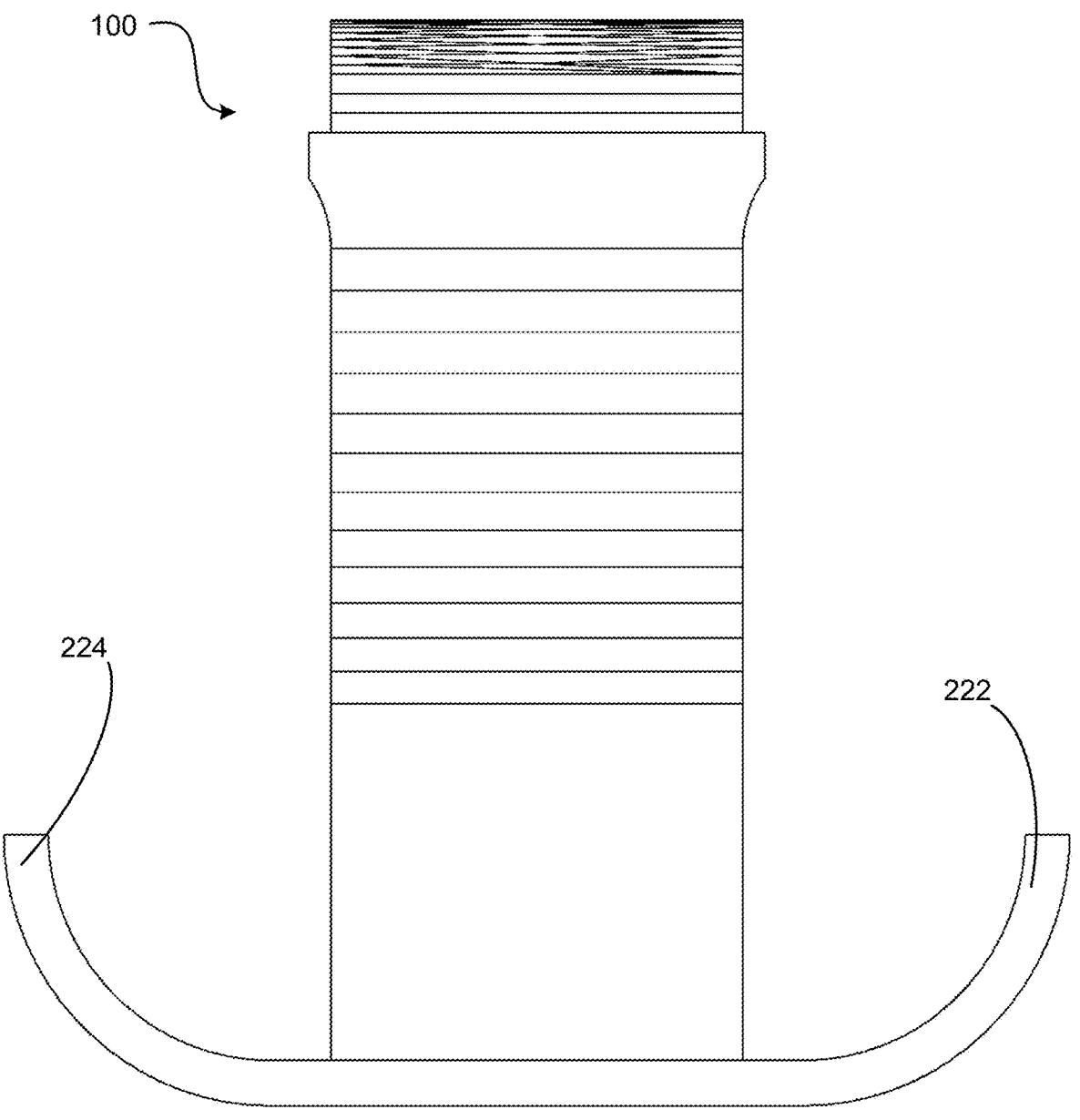
FIG. 8 is a top view of a respiratory interface device in accordance with various embodiments of the present disclosure.
Figure 9:
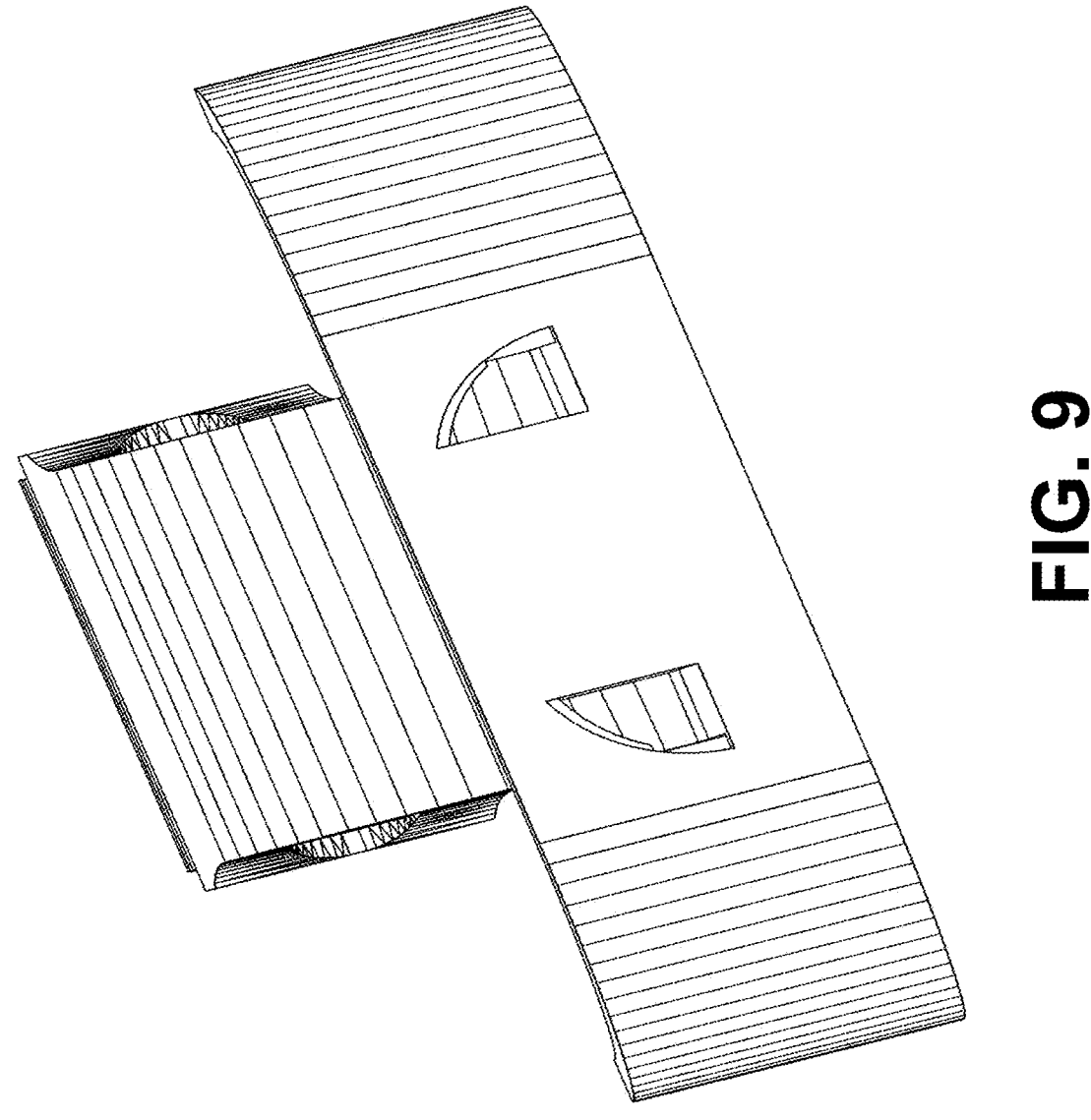
FIG. 9 is a front view of a respiratory interface device in accordance with various embodiments of the present disclosure.

As shown in FIG. 1, the dental plate 200 comprises an upper lip engaging portion 202 that extends upward from a distal portion of the dental plate 200 and a lower lip engaging portion 204 that extends downward from the distal portion of the dental plate 200. The dental plate 200 further comprises a first side flange portion 222 that extends from the dorsal portion of the dental plate 200 toward a first side (e.g., left side) of the dental plate 200, curving rearward in the direction of the bridge portion 300. In some examples, the dental plate 200 further comprises a second side flange portion 224 that extends from the dorsal portion of the dental plate 200 toward a second side (e.g., right side) of the dental plate 200, curving rearward in the direction of the bridge portion 300. Referring briefly to FIG. 8, in the example shown in this figure, the dental plate 200 is substantially C-shaped.

Referring back to FIG. 1, in particular embodiments, the upper lip engaging portion 202 is configured to engage an upper lip of a patient when the respiratory interface device 100 is inserted into the patient's mouth. Similarly, in some embodiments, the lower lip engaging portion 204 is configured to engage a lower lip of the patient when the respiratory interface device 100 is inserted into the patient's mouth. In some embodiments, engagement of the upper and lower lip may include the upper lip engaging portion 202 and the lower lip engaging portion 204 being positioned in front of the patient's lips when the respiratory interface device 100 is inserted into the patient's mouth. In other embodiments, engagement of the upper and lower lip may include the upper lip engaging portion 202 and the lower lip engaging portion 204 being positioned behind the patient's lips when the respiratory interface device 100 is inserted into the patient's mouth. In some embodiments, the dental plate 200 has a height and/or thickness of about 1 cm. In various embodiments, the dental plate 200 has a width of about 3 cm. In various embodiments, the length of the c-shaped curve of the plate is about 5.7 cm.

In some embodiments, the first side flange portion 222 and the second side flange portion 224 may substantially follow a curve of the patient's teeth and/or alveolar ridge if the patient is edentulous (i.e., such that the first side flange portion 222 and the second side flange portion 224 are positioned adjacent the patient's teeth when the respiratory interface device 100 is in the patient's mouth, either in front of or behind the patient's lips).

Figure 2:
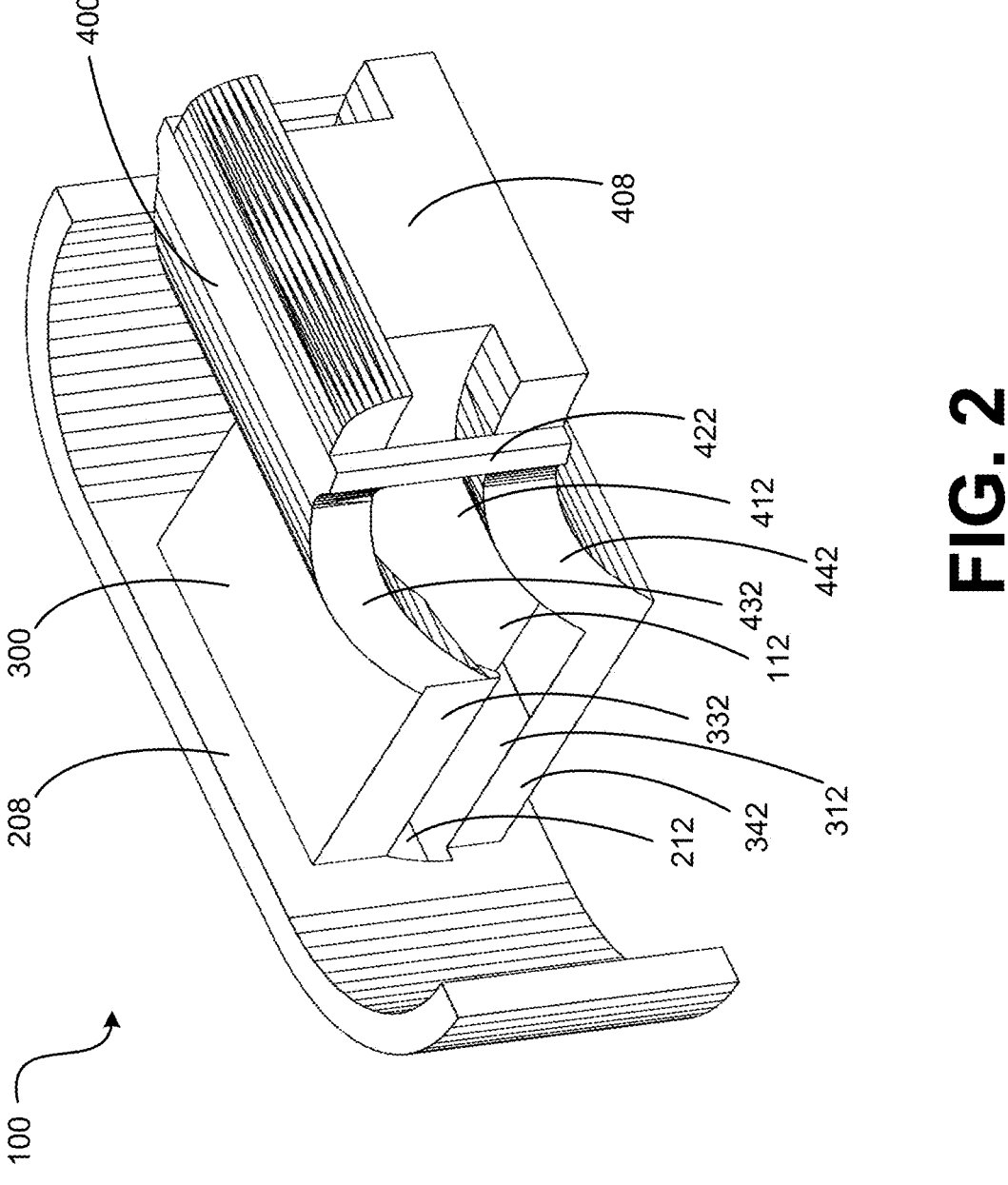
FIG. 2 is a rear perspective view of the respiratory interface device shown in FIG. 1.

In various embodiments, as may be understood from FIGS. 1 and 2, the dental plate 200 defines a front face 206 and a rear face 208. In particular embodiments, the dental plate 200 defines a first conduit receiving cutout 212 and a second conduit receiving cutout 214. Each of the first conduit receiving cutout 212 and the second conduit receiving cutout 214 extend through the dental plate 200 from the front face 206 to the rear face 208. In the embodiment shown in these figures, the first conduit receiving cutout 212 and the second conduit receiving cutout 214 are spaced apart. In the embodiment shown in these figures, each of the first conduit receiving cutout 212 and the second conduit receiving cutout 214 are substantially quarter-circle (e.g., quadrant) shaped. In other embodiments, each of the first conduit receiving cutout 212 and the second conduit receiving cutout 214 may have any other suitable shape (e.g., round, circular, square, rectangular, etc.). In various embodiments each of the first conduit receiving cutout 212 and the second conduit receiving cutout 214 are sized to receive at least one conduit (e.g., a tube). In some embodiments, each of the first conduit receiving cutout 212 and the second conduit receiving cutout 214 are sized to receive a substantially standard sized nasal cannula tube. In other embodiments, the first conduit receiving cutout 212 and the second conduit receiving cutout 214 are configured to receive any suitable tubing.

In some embodiments, each of the first conduit receiving cutout 212 and the second conduit receiving cutout 214 are sized to receive a conduit such that the conduit fits sufficiently snuggly in the first conduit receiving cutout 212 or the second conduit receiving cutout 214 to maintain the conduit in a substantially fixed position relative to the respiratory interface device 100, and sufficiently loosely to enable a user to insert the conduit through the first conduit receiving cutout 212 or the second conduit receiving cutout 214 as will be described more fully below.

In some embodiments (not pictured), the first conduit receiving cutout 212 and the second conduit receiving cutout 214 may define a single cutout configured to receive two or more conduits (e.g., tubes). In such embodiments, the two conduits may be inserted through the single cutout, and then separated into the first conduit channel 112 and the second conduit channel 114 which are described more fully below. In still other embodiments, the respiratory interface device 100 comprises a single cutout and channel that extends through the respiratory interface device. In still other embodiments, the respiratory interface device 100 comprises a plurality of channels that extend through the device to provide an oxygen delivery and carbon dioxide return pathway.

Referring to FIGS. 1-4, in various embodiments, the bridge portion 300 extends from the rear face 208 of the dental plate 200 substantially rearward. As may be understood from these figures, the bridge portion 300 is substantially rectangular and defines a superior face 302 and an inferior face 304. In various embodiments, the bridge portion 300 has a thickness of about 1 cm. As may be understood from this disclosure, a patient may bite down on the superior face 302 and the inferior face 304 of the bridge portion 300 when the respiratory interface device 100 is inserted into the patient's mouth. As such, in particular embodiments, the bridge portion 300 (and the respiratory interface device 100) comprise a material that is sufficiently rigid (e.g., stiff) to protect the device 100 and the various components thereof against compression or occlusion due to the structure of the patient's oral cavity or mastication of the device. In other embodiments, the bridge portion 300 (and the respiratory interface device 100) comprise a material that is sufficiently soft, smooth, flexible, etc. so as to not injure an oral cavity mucosa of the patient while the device 100 is in the patient's mouth. In some embodiments, one or more portions of the device 100 comprise thermoplastic polymer, thermoplastic polyester, thermoplastic elastomer, silicone, or other suitable material or combination thereof. In some embodiments, the device 100 and any suitable portion thereof may include any suitable material.

As may be understood from FIG. 2, the bridge portion 300 comprises a first bridge portion upper flange 332 that extends substantially perpendicularly outward from an upper portion of the first side of the bridge portion 300. The bridge portion 300 further comprises a first bridge portion lower flange 342 that extends substantially perpendicularly outward from a lower portion of the first side of the bridge portion 300. As may be understood from this figure and from FIG. 5, the first bridge portion upper flange 332 and the first bridge portion lower flange 342 are spaced apart and substantially perpendicular to one another. In some embodiments, the first bridge portion upper flange 332 and the first bridge portion lower flange 342 define a first bridge portion conduit channel portion 312 therebetween. In various examples, the first bridge portion conduit channel portion 312 is configured to at least temporarily house a conduit (e.g., tube) adjacent to the first side of the bridge portion 300 when the conduit is inserted into the respiratory interface device 100.

Although the first bridge portion conduit channel portion 312 is shown in these embodiments as being open (e.g., is defined by the bridge portion 300, the first bridge portion upper flange 332, and the first bridge portion lower flange 342 on three sides), it should be understood that, in other embodiments, the first bridge portion conduit channel portion 312 may be at least partially enclosed (e.g., fully enclosed).

Figure 3:
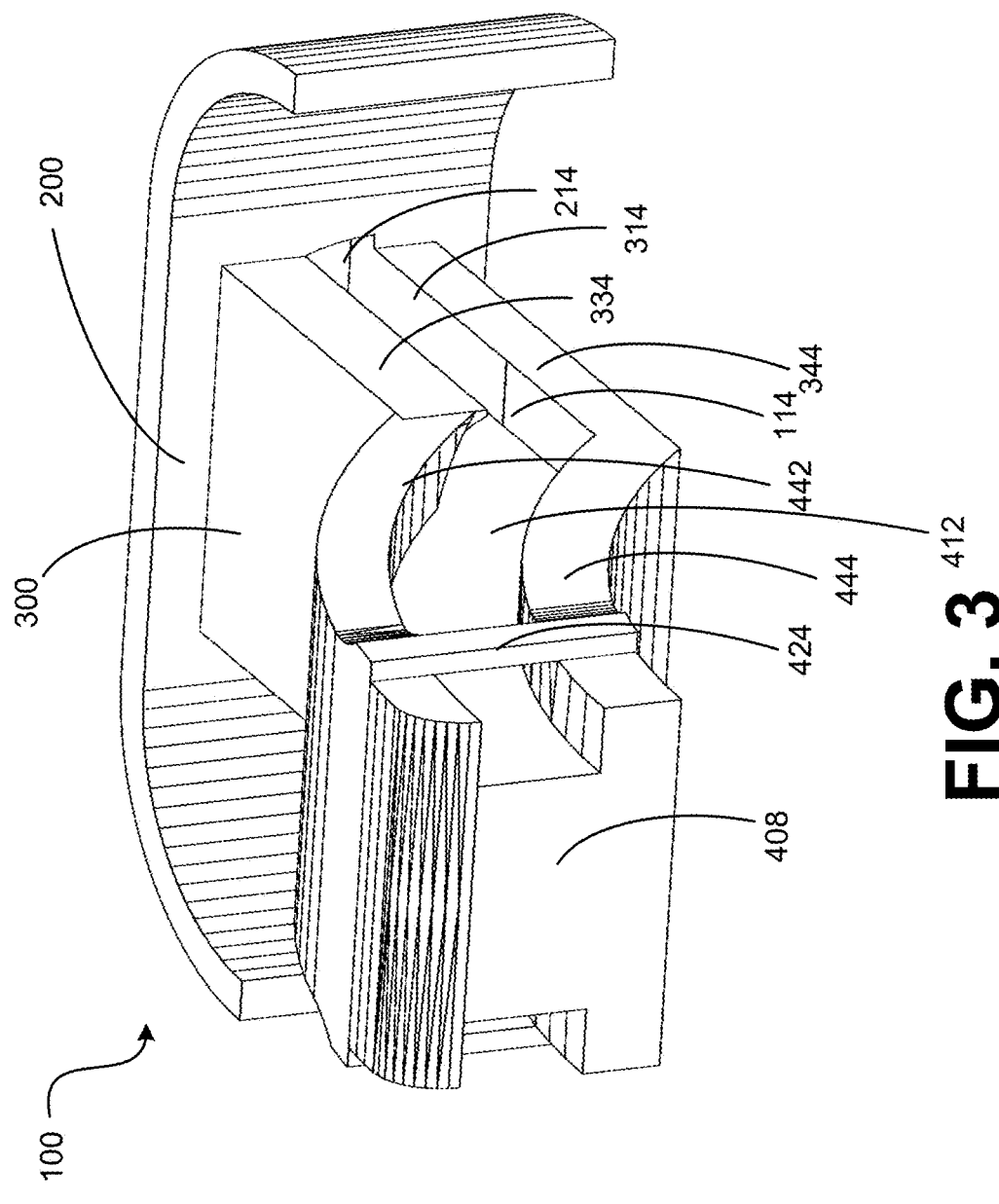
FIG. 3 is a second rear perspective view of the respiratory interface device shown in FIG. 1.
Figures 4, 5:
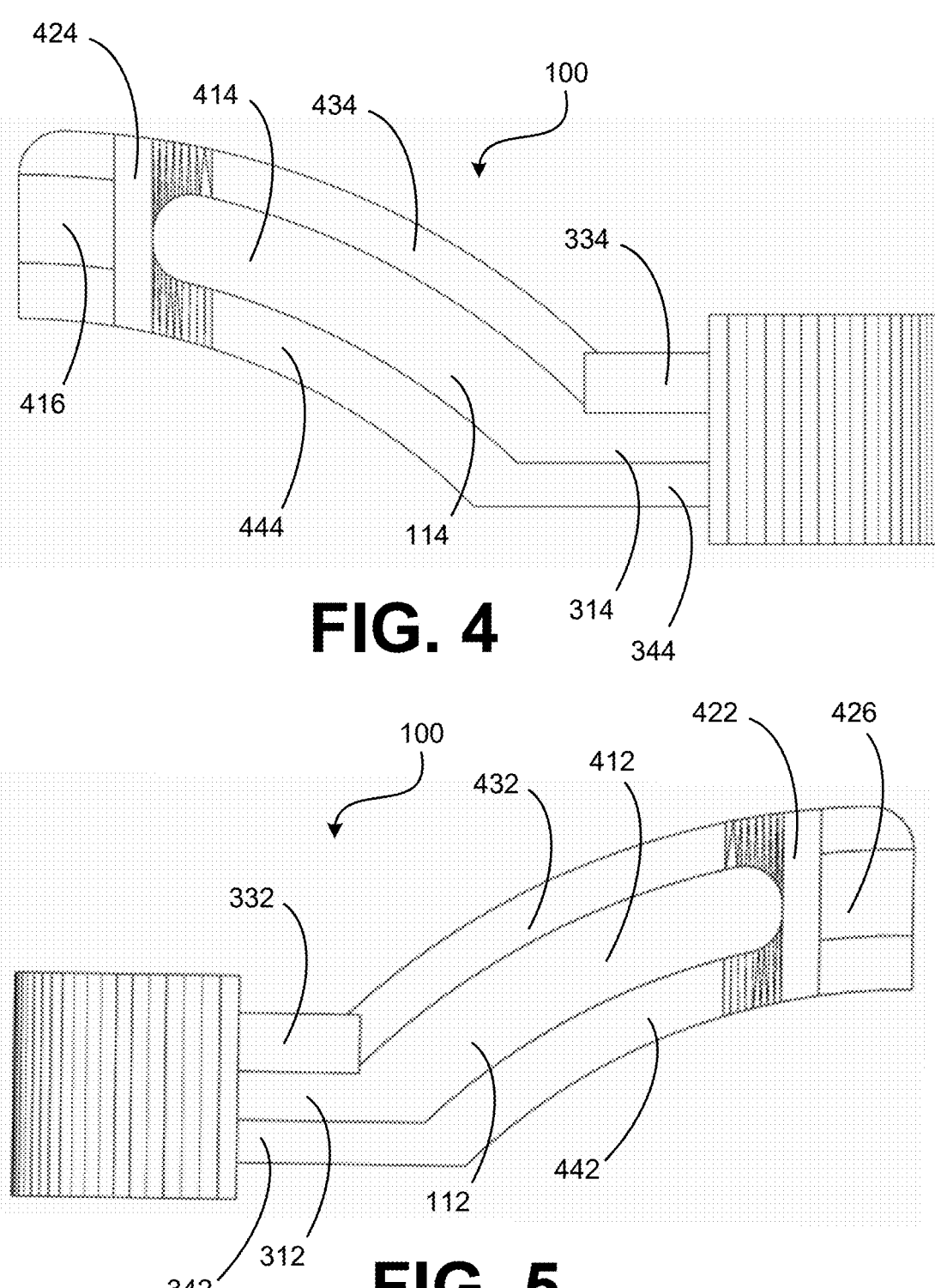
FIG. 4 is a first side view of a respiratory interface device in accordance with various embodiments of the present disclosure.
FIG. 5 is a second side view of a respiratory interface device in accordance with various embodiments of the present disclosure.
Figure 6:
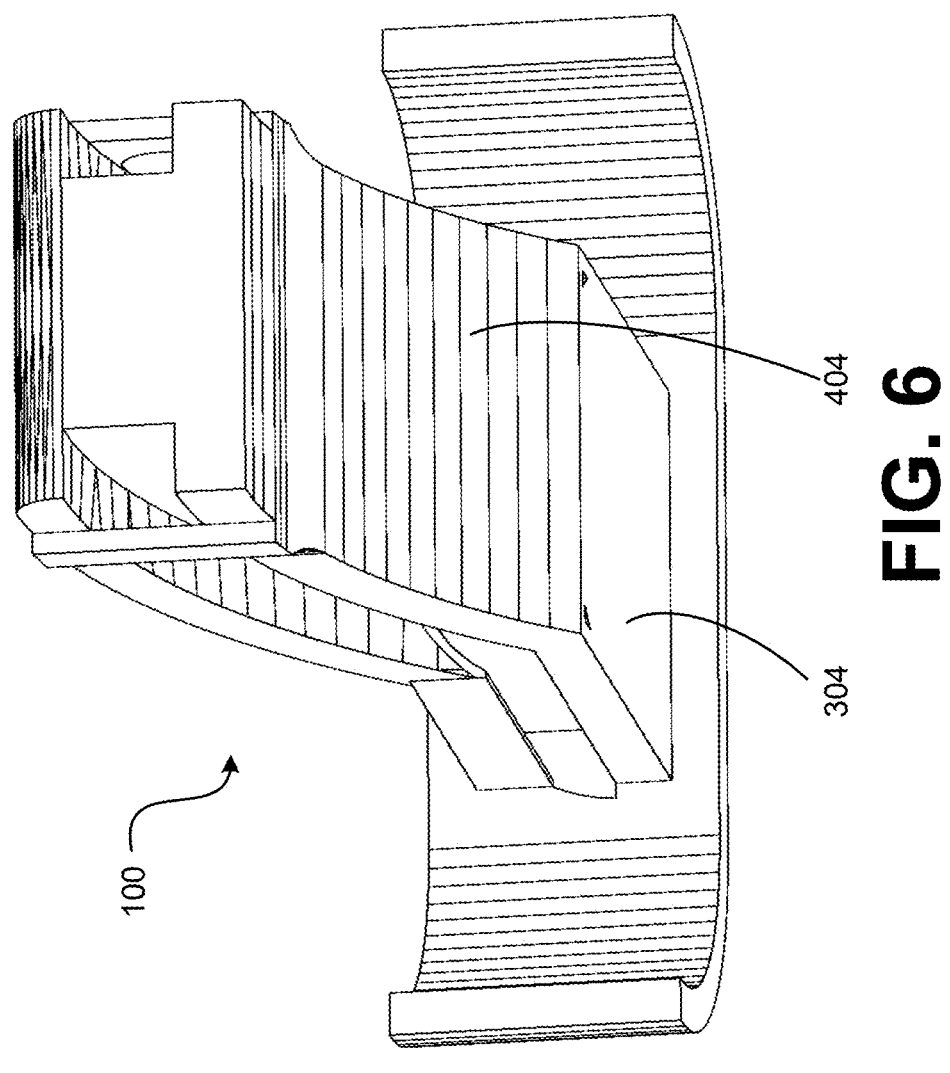
FIG. 6 is a rear perspective view of a respiratory interface device in accordance with various embodiments of the present disclosure.
Figure 7:
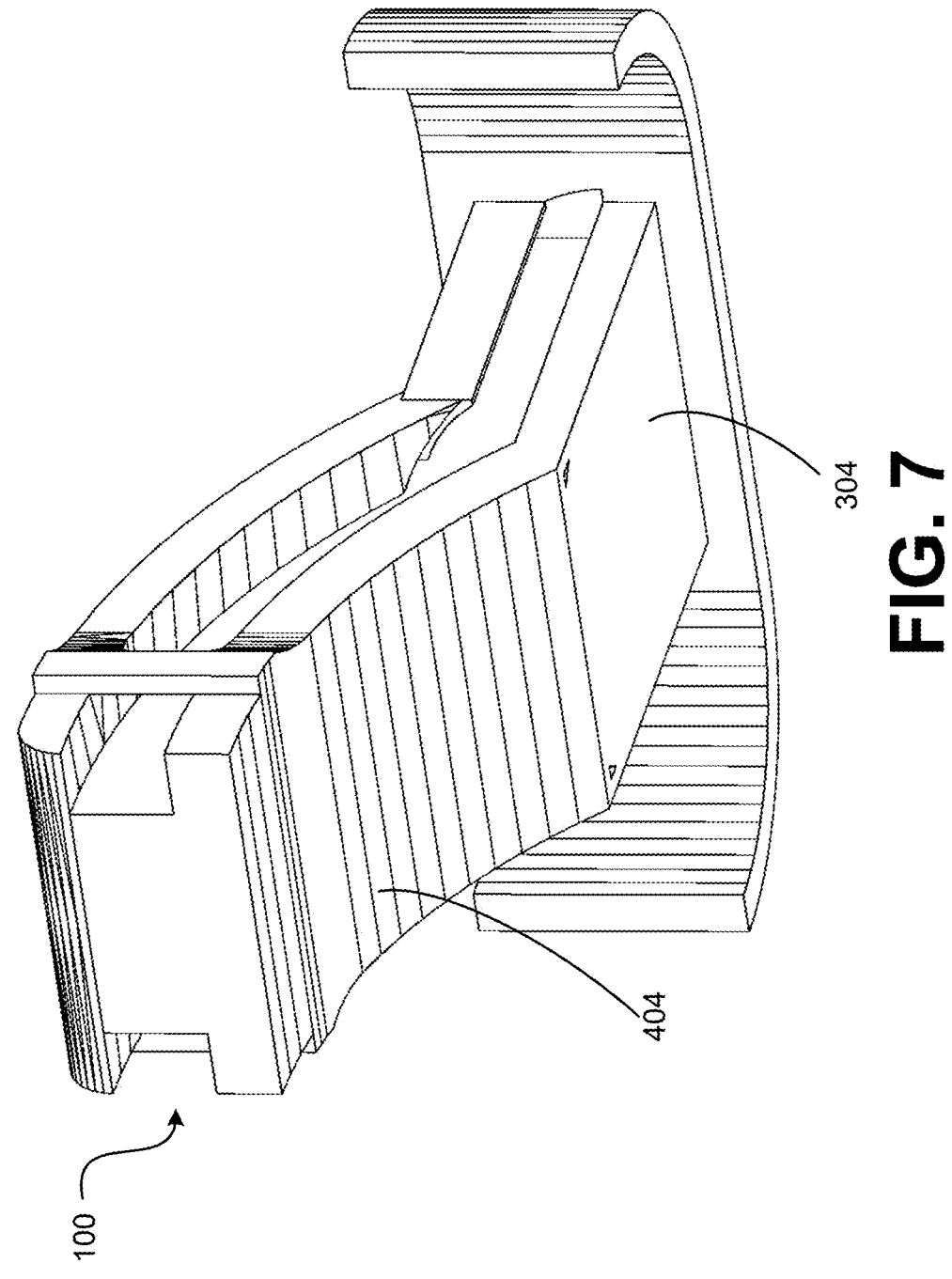
FIG. 7 is a rear perspective view of a respiratory interface device in accordance with various embodiments of the present disclosure.

As may be further understood from FIG. 3, the bridge portion 300 further comprises a second bridge portion upper flange 334 that extends substantially perpendicularly outward from an upper portion of the second side of the bridge portion 300. The bridge portion 300 further comprises a second bridge portion lower flange 344 that extends substantially perpendicularly outward from a lower portion of the second side of the bridge portion 300. As may be understood from this figure and from FIG. 4, the second bridge portion upper flange 334 and the second bridge portion lower flange 344 are spaced apart and substantially perpendicular to one another. In some embodiments, the second bridge portion upper flange 334 and the second bridge portion lower flange 344 define a second bridge portion conduit channel portion 314 therebetween. In various examples, the second bridge portion conduit channel portion 314 is configured to at least temporarily house a second conduit (e.g., tube) adjacent to the second side of the bridge portion 300 when the conduit is inserted into the respiratory interface device 100.

As with the first bridge portion conduit channel portion 312, although the second bridge portion conduit channel portion 314 is shown in these embodiments as being open (e.g., is defined by the bridge portion 300, the second bridge portion upper flange 334, and the second bridge portion lower flange 344 on three sides), it should be understood that, in other embodiments, the second bridge portion conduit channel portion 314 may be at least partially enclosed (e.g., fully enclosed). As further discussed above, in still other embodiments, the device 100 may comprise only a single bridge portion conduit channel portion or a plurality (i.e., more than two) bridge portion channels.

In some embodiments, the airway arch 400 arcs upward and rearward from a rear portion of the bridge portion 300. In various embodiments, the airway arch 400 does not arc back downward following the upward arc. This lack of downward arching may, for example, prevent interference with the patient's pharynx and/or soft palate and distinguishes the airway arch 400 from traditional oropharyngeal airways.

As may be understood from FIGS. 1-5, the airway arch 400, in some embodiments, is shaped as a substantially elliptical quadrant. In particular embodiments, the airway arch 400 is shaped such that the portion of the airway arch 400 adjacent the bridge portion 300 is disposed below an end portion of the airway arch 400 adjacent the back face 408 when the device 100 is oriented in the manner shown in FIGS. 4 and 5. Such a configuration is distinguishable from current oropharyngeal airways in which the end portion of the oropharyngeal airway arcs upward and back down such that the end portion is disposed below starting point of the airway arch when in such an orientation. As will be appreciated by one skilled in the art, current oropharyngeal airways are designed to be used when a patient is fully sedated and/or without protective airway reflex. As such, current oropharyngeal airways would never be used on conscious or semi-conscious patients as they are designed to displace the tongue forward, holding it away from the posterior pharyngeal wall, and extend at least partially into a patient's throat/pharynx to provide oxygen and/or ventilation. In a patient that is not unconscious, such a design would trigger the protective airway reflexes and not be tolerable or suitable for the situation.

In some embodiments, the airway arch 400 is configured to be positioned in a patient's mouth. In various embodiments, the airway arch 400 defines a superior portion 402 configured to engage at least a portion of a patient's palate when the respiratory interface device 100 is inserted in the patient's mouth. The airway arch 400 further defines an inferior portion 404 that may be configured to engage at least a portion of the patient's tongue when the respiratory interface device 100 is inserted in the patient's mouth. In some embodiments, the airway arch 400 is dimensioned (i.e., has a length) such that the back face 408 of the airway arch 400 is abutting the hard palate of the patient when the respiratory interface device 100 is inserted in the patient's mouth. In other embodiments, the airway arch 400 extends about ⅔rds the length of the patient's palate when the respiratory interface device 100 is inserted in the patient's mouth. In particular embodiment, the airway arch 400 has a length of between about 19 mm and about 31 mm. In still other embodiments, the airway arch has a length of up to about 60 mm. In some embodiments, the airway arch 400 has a length of about 33 mm.

In some embodiments, the airway arch 400 is dimensioned to have a height such that the respiratory interface device 100 does not interfere with the patient's lips or tongue when the respiratory interface device 100 is inserted in the patient's mouth. In particular, the height may substantially correspond to a height of a palatal depth of a patient. In some examples, the height may be up to about 25 mm. In a particular embodiment, the height is about 21 mm. In still other examples, the height may be between about 15 mm and 20 mm. In still other embodiments, the height may be less than 15 mm. In particular embodiments, the airway arch 400 may have any suitable height and length to accommodate patients with different sized mouths. In some embodiments, when using a respiratory interface device 100, a provider may select a size of the device 100 that most closely matches the patients' palatal depth and distance to a point substantially ⅔rds distance back on the patient's hard palate. In this way, the airway arch 100 may engage at least a portion of the patient's palate when inserted into the patient's mouth, without activating the patient's protective airway reflexes by extending too far into the patient's mouth or interfering with the patient's tongue.

Returning to FIG. 1, the airway arch 400 comprises a first airway arch upper flange 432 that extends substantially perpendicularly outward from an upper portion of the first side of the airway arch 400. The airway arch 400 further comprises a first airway arch lower flange 442 that extends substantially perpendicularly outward from a lower portion of the first side of the airway arch 400. As may be understood from this figure and from FIG. 5, the first airway arch upper flange 432 and the first airway arch lower flange 442 are spaced apart from one another. In some embodiments, the first airway arch upper flange 432 and the first airway arch lower flange 442 define a first airway arch conduit channel portion 412 therebetween. In various examples, the first airway arch conduit channel portion 412 is configured to at least temporarily house a conduit (e.g., tube) adjacent the first side of the airway arch 400 when the conduit is inserted into the respiratory interface device 100. In some embodiments, the first airway arch upper flange 432 extends the first bridge portion upper flange 332 of the bridge portion 300 to form a substantially continuous flange (e.g., lip). Similarly, in some embodiments, the first airway arch lower flange 442 extends the first bridge portion lower flange 342 of the bridge portion 300 to form a substantially continuous flange (e.g., lip).

In some embodiments, the airway arch 400 comprises a first conduit stabilizing bar 422 that extends from the first airway arch upper flange 432 to the first airway arch lower flange 442 adjacent a rear portion of the airway arch 400. In some embodiments, the first conduit stabilizing bar 422 is configured to maintain the conduit (e.g., tube) within the first airway arch conduit channel portion 412 when the conduit is inserted into the respiratory interface device 100. In various embodiments, the airway arch 400 defines a first conduit distal end support portion 426 adjacent the back face 408. In some embodiments, the first conduit distal end support portion 426 is defined by the first conduit stabilizing bar 422. In various embodiments, the airway arch 400 is configured such that the distal end of the conduit is positioned in the first conduit distal end support portion 426. In this way, the respiratory interface device 100 may provide airflow at the first conduit distal end support portion 426 such that the conduit end is optimally positioned for oxygen delivery. In various embodiments, the first conduit stabilizing bar 422 may extend along a full length of the first conduit stabilizing bar 422 such that the first airway arch conduit channel portion 412 is at least partially enclosed (e.g., fully enclosed).

In some embodiments, the airway arch 400 further comprises a second airway arch upper flange 434 that extends substantially perpendicularly outward from an upper portion of the second side of the airway arch 400. The airway arch 400 further comprises a second airway arch lower flange 444 that extends substantially perpendicularly outward from a lower portion of the second side of the airway arch 400. As may be understood from this figure and from FIG. 4, the second airway arch upper flange 434 and the second airway arch lower flange 444 are spaced apart from one another. In some embodiments, the second airway arch upper flange 434 and the second airway arch lower flange 444 define a second airway arch conduit channel portion 414 therebetween. In various examples, the second airway arch conduit channel portion 414 is configured to at least temporarily house a conduit (e.g., tube) adjacent the second side of the airway arch 400 when the conduit is inserted into the respiratory interface device 100. In some embodiments, the second airway arch upper flange 434 extends the second bridge portion upper flange 334 of the bridge portion 300 to form a substantially continuous flange (e.g., lip). Similarly, in some embodiments, the second airway arch lower flange 444 extends the second bridge portion lower flange 344 of the bridge portion 300 to form a substantially continuous flange (e.g., lip).

In some embodiments, the airway arch 400 comprises a second conduit stabilizing bar 424 that extends from the second airway arch upper flange 434 to the second airway arch lower flange 444 adjacent a rear portion of the airway arch 400. In some embodiments, the second conduit stabilizing bar 424 is configured to maintain the conduit (e.g., tube) within the second airway arch conduit channel portion 414 when the conduit is inserted into the respiratory interface device 100. In various embodiments, the airway arch 400 defines a second conduit distal end support portion 416 adjacent the back face 408. In some embodiments, the second conduit distal end support portion 416 is defined by the second conduit stabilizing bar 424. In various embodiments, the airway arch 400 is configured such that the distal end of the second conduit is positioned in the second conduit distal end support portion 416. In this way, the respiratory interface device 100 may provide airflow at the second conduit distal end support portion 416 such that the conduit end is optimally positioned for oxygen delivery. In various embodiments, the second conduit stabilizing bar 424 may extend along a full length of the second conduit stabilizing bar 424 such that the second airway arch conduit channel portion 414 is at least partially enclosed (e.g., fully enclosed).

In various embodiments, the first conduit receiving cutout 212, the first bridge portion conduit channel portion 312, and the first airway arch conduit channel portion 412 define a substantially continuous first conduit channel 112 through which a conduit tube is inserted until an end of the tube reaches the first conduit distal end support portion 426. In other embodiments, the first conduit channel 112 may provide a channel through which air can flow (either through or out of the respiratory interface device 100) without any internal conduit, tubing, etc. In such embodiments, external conduit or tubing may at least temporarily couple to an entrance of the first conduit channel 112 (e.g., the first conduit receiving cutout 212). 2 Similarly, in some embodiments, the second conduit receiving cutout 214, the second bridge portion conduit channel portion 314, and the second airway arch conduit channel portion 414 define a substantially continuous second conduit channel 114 through which a conduit tube is inserted until an end of the tube reaches the second conduit distal end support portion 416. In other embodiments, the second conduit channel 114 may provide a channel through which air can flow (either through or out of the respiratory interface device 100) without any internal conduit, tubing, etc. In such embodiments, external conduit or tubing may couple to an entrance of the second conduit channel 113 (e.g., the second conduit receiving cutout 214).

Figure 10:
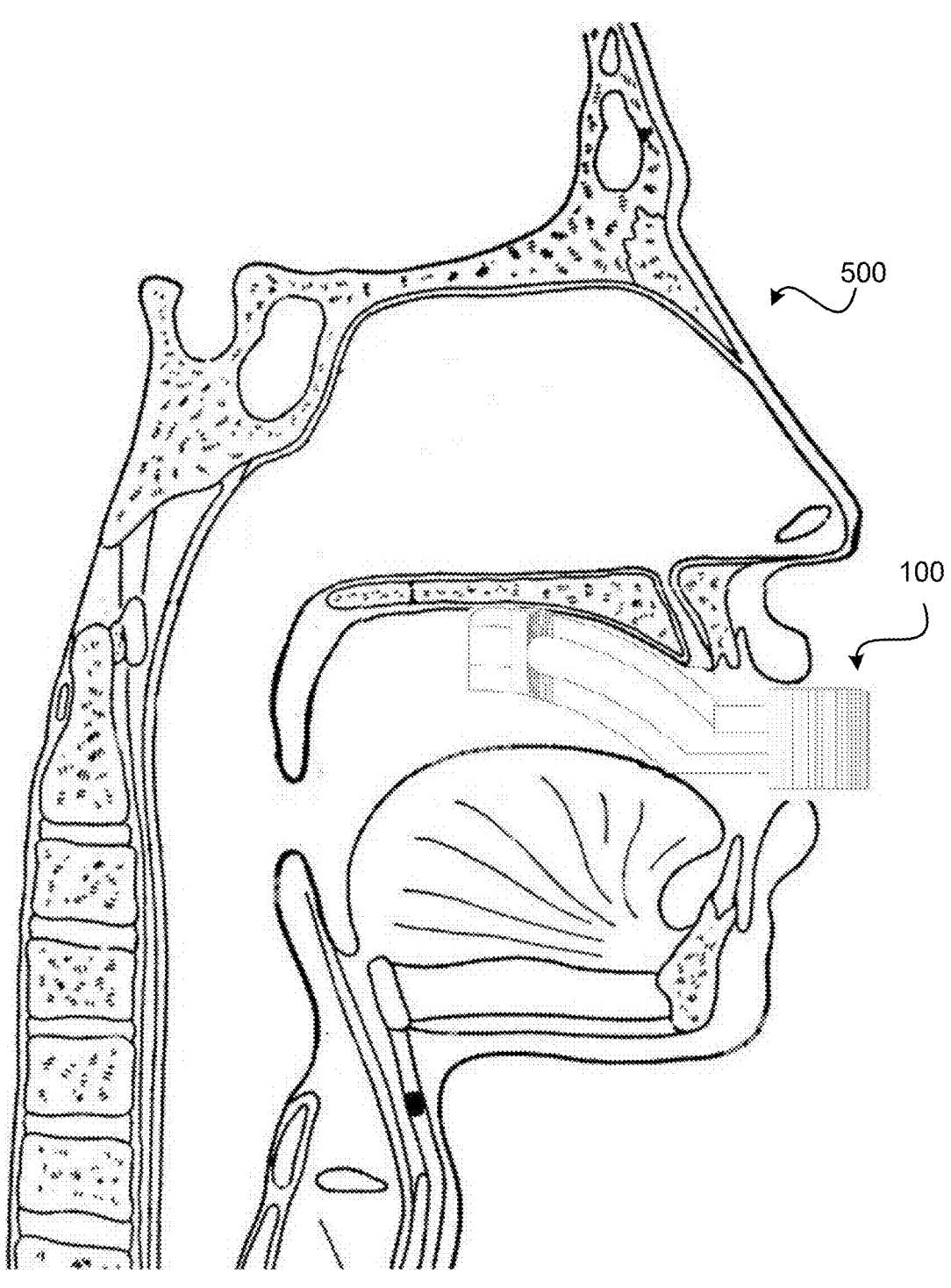
FIG. 10 is a side cutaway view of a patient with a respiratory interface device inserted into their mouth.

FIG. 10 depicts a patient 500 with the respiratory interface device 100 inserted into their mouth. As may be understood from this figure, an end of the device 100 extends into the patient's mouth until about two-thirds back on the hard palate. In this way, the device 100 does not substantially interfere with the patient's tongue or reach far enough back to trigger a protective airway reflex.

Figure 11:
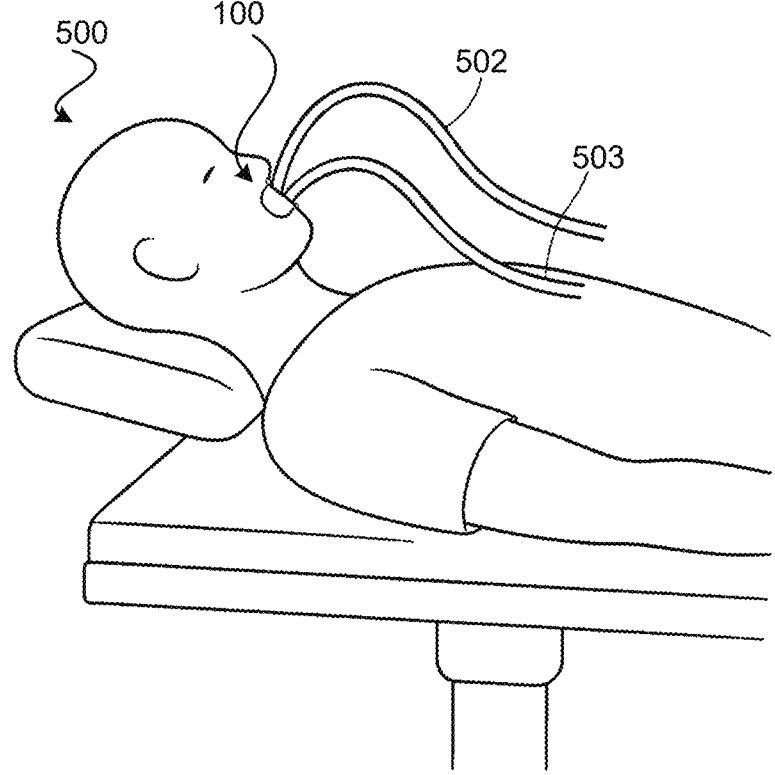
FIG. 11 is a side view of a patient with a respiratory interface device inserted into their mouth.

In practice, a user may use the tubing from an End-Tidal Co2 nasal cannula, which has one tubing for oxygen delivery and another for CO2 sampling (e.g., by cutting the tubes from the traditional End-tidal Co2 nasal cannula). The user may then insert the first tube into the first conduit receiving cutout 212, through the first bridge portion conduit channel portion 312 and the first airway arch conduit channel portion 412, until an end of the conduit (e.g., tubing) is positioned at the first conduit distal end support portion 426 supported by the first conduit stabilizing bar 422. Similarly, the user may insert the second tube into the second conduit receiving cutout 214, and through the second bridge portion channel portion 314 and the second airway arch conduit channel portion 414, until an end of the second conduit tube is positioned at the second conduit distal end support portion 416 supported by the second conduit stabilizing bar 424. The user may then place the respiratory interface device 100 into the patient's mouth to deliver oxygen through the two tubes during a medical procedure (e.g., facial surgery). FIG. 11 depicts a patient 500 with the respiratory interface device 100 inserted in their mouth during a procedure. As may be understood from this figure, a first conduit 502 and second conduit 503 are at least temporarily coupled to the respiratory interface device 100. In some embodiments, temporarily coupling the first and second conduit 502, 503 may include inserting each of the first and second conduit 502, 503 through respective channels of the respiratory interface device 100. In other embodiments, coupling the first and second conduit 502, 503 may include coupling each of the first and second conduit 502, 503 to respective channel openings of the respiratory interface device 100 (e.g., defined in the dental plate 200). In other embodiments, the first and second conduit 502, 503 may be coupled and/or inserted into the respiratory interface device 100 in any other suitable manner. In particular embodiments, the first and second conduit 502, 503 may include one tubing for oxygen delivery and another for CO2 sampling.

In various embodiments, the user (e.g., provider) places the respiratory interface device such that it does not interfere with the patient's tongue and/or trigger a protective airway reflex in the patient.

Pilot Study:

A minimal viable prototype (MVP) was developed and approved to be tested on up to 20 patients at the University of Virginia. Testing was completed under full IRB approval #HSR220400. The MVP was printed using thermoplastic polyurethane (TPU) on the Mini 3 LutzBot 3D Printer.

The objective for this pilot research study is to determine the comfort and usefulness of the trans-oral 3D-printed respiratory interface device to provide oxygenation and ventilation, while minimally disrupting facial architecture during facial plastic surgery performed under monitored anesthesia care (MAC). Tubing from the end-tidal CO2 nasal cannula was used by cutting the tubing away from the nasal cannula. The tubing used to deliver oxygen was inserted into one channel and the tubing used to sample CO2 was inserted into the other channel.

The primary outcomes are the minimum percentage oxygen saturation observed throughout, as measured with standard pulse oximetry that is routinely monitored during surgery. Secondary outcomes will include number of repositionings required, number of breaches in sterile technique, and satisfaction of the anesthesiologist and surgeon and oral cavity exam of the patient after the surgery.

In summary, 20 patients undergoing facial surgery under monitored anesthesia care (MAC) have been tested. Key findings include the following:

a. 15/20 surgeries did not require any adjustment of the oropharyngeal airway device b. Breaking of sterility to adjust the device only occurred in 10% (2 of 20) cases c. The average duration of surgery was 52.2 minutes±0.01 d. The average oxygen reported during surgery was 94.8%±2.9 e. One hundred percent (%) of anesthesia users reported they would use the device again for a future MAC case f. No patient experienced any bleeding or injury to the oral cavity with device use g. The average score reported by surgeons for improved surgical efficiency was 4.5 on a 1-5 scale.

It should be emphasized that the above-described examples of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A respiratory interface device comprising:
a dental plate defining at least one conduit receiving cutout;
a bridge portion extending rearward from the dental plate;
a bridge portion upper flange that extends outward from an upper portion of a first side of the bridge portion from the dental plate;
a bridge portion lower flange that extends outward from a lower portion of the first side of the bridge portion from the dental plate spaced apart from the bridge portion upper flange;
an elliptical quadrant shaped airway arch arcing from the bridge portion from an opposing portion of the bridge portion from the dental plate, the airway arch defining an air outlet on a back face of the airway arch, wherein the respiratory interface device defines at least one channel that extends from the at least one conduit receiving cutout, through the bridge portion and the airway arch, and terminating at the air outlet;
an airway arch upper flange that extends outward from an upper portion of the first side of the airway arch;
an airway arch lower flange that extends outward from a lower portion of the first side of the airway arch spaced apart from the airway arch upper flange; and
a conduit stabilizing portion that extends from the airway arch upper flange to the airway arch lower flange adjacent a rear portion of the airway arch, wherein:
the at least one channel is configured to receive at least one conduit through the at least one conduit receiving cutout and maintain an end of the at least one conduit adjacent the air outlet;
the bridge portion upper flange, the airway arch upper flange, the bridge portion lower flange, and the airway arch lower flange define the at least one channel;
the conduit stabilizing portion is configured to maintain the end of the at least one tubing adjacent the oxygen outlet within the at least one channel, and
the at least one channel is at least partially enclosed and at least partially open.

2. The respiratory interface device of claim 1, wherein the air outlet is disposed at a height greater than the at least one conduit receiving cutout when the respiratory interface device is in a neutral position with the bridge portion parallel to the ground.

3. The respiratory interface device of claim 1, wherein the airway arch is configured to engage a hard palate of a patient when inserted into a mouth of the patient without triggering a protective airway reflex of the patient.

4. The respiratory interface device of claim 3, wherein the dental plate is configured to at least partially engage at least a portion of one or more lips, teeth, or alveolar ridge of the patient to maintain the respiratory interface device at a desired distance into the mouth of the patient.

5. The respiratory interface device of claim 1, wherein the respiratory interface device comprises at least one of thermoplastic polyurethane or thermoplastic elastomer.

6. The respiratory interface device of claim 1, wherein the conduit stabilizing bar defines at least a portion of the at least one channel that is partially enclosed.

7. The respiratory interface device of claim 1, wherein the dental plate has a height of up to about 1.5 cm.

8. A respiratory interface device for a patient, the respiratory interface device comprising:
a dental plate defining a front face and a rear face;
a bridge portion extending rearward from the rear face of the dental plate, the bridge portion comprising:
a bridge portion upper flange that extends outward from an upper portion of a first side of the bridge portion from the dental plate; and
a bridge portion lower flange that extends outward from a lower portion of the first side of the bridge portion from the dental plate spaced apart from the bridge portion upper flange; and
an airway arch arcing from the bridge portion from an opposing portion of the bridge portion from the dental plate, the airway arch comprising:
an airway arch upper flange that extends outward from an upper portion of the first side of the airway arch;
an airway arch lower flange that extends outward from a lower portion of the first side of the airway arch spaced apart from the airway arch upper flange; and
a conduit stabilizing bar that extends from the airway arch upper flange to the airway arch lower flange adjacent a rear portion of the airway arch, wherein:
the respiratory interface device defines at least one partially open channel that extends from the front face of the dental plate through the bridge portion and the airway arch and terminates at a rear portion of the airway arch, the at least one partially open channel defined by the airway arch upper flange, the airway arch lower flange, the bridge portion upper flange, and the bridge portion lower flange;
an end of the at least one channel is disposed substantially adjacent the mark that is substantially ⅔rds back on the hard palate of the patient when the respiratory interface device is placed in the mouth of the patient;
the at least one partially open channel is configured to receive and at least temporarily maintain at least one conduit through the at least one partially open channel from the dental plate to the rear portion of the airway arch; and
the conduit stabilizing bar is configured to maintain an end of the at least one conduit adjacent the rear portion of the airway arch within the at least one partially open channel.

9. The respiratory interface device of claim 8, wherein the at least one partially open channel comprises a first channel and a second channel and each of the first channel and the second channel are each configured to respectively receive and at least temporarily maintain at least a portion of at least one conduit, the at least one conduit comprising a first tubing for oxygen delivery and a second tubing for carbon dioxide sampling.

10. The respiratory interface device of claim 8, wherein the airway arch has a shape that is an elliptical quadrant.

11. The respiratory interface device of claim 8, wherein the airway arch is configured to engage at least a portion of the hard palate of the patient when the respiratory interface device is placed in the mouth of the patient.

12. The respiratory interface device of claim 8, wherein the airway arch is configured to extend into the mouth of the patient sufficiently far to provide oxygen through the at least one partially open channel in a desired position within the mouth without triggering a protective airway reflex of the patient.

13. The respiratory interface device of claim 8, wherein the respiratory interface device comprises a biocompatible material including one or more of silicone, thermoplastic elastomer, polyurethane, or medical-grade rubber selected depending on a desired rigidity, flexibility, or transparency of the respiratory interface device.

14. The respiratory interface device of claim 8, wherein:
  the dental plate comprises an upper lip engaging portion that extends upward from a distal portion of the dental plate and a lower lip engaging portion that extends downward from the distal portion of the dental plate; and
  the dental plate is c-shaped.

15. The respiratory interface device of claim 14, wherein the dental plate has a height that is about 1.5 times a height of the bridge portion.

16. The respiratory interface device of claim 8, wherein the respiratory interface device is sufficiently rigid such that a biting force from the patient when the respiratory interface device is in the mouth of the patient does not deform the at least one partially open channel.

17. A method of delivering oxygen to a patient or monitoring carbon dioxide from a patient during a medical procedure, the method comprising:
  providing a respiratory interface device comprising:
    a dental plate defining a front face, a rear face, and an oxygen inlet;
    an airway arch arcing from the rear face of the dental plate and defining an oxygen outlet;

an airway arch upper flange that extends outward from an upper portion of a first side of the airway arch;
    an airway arch lower flange that extends outward from a lower portion of the first side of the airway arch spaced apart from the airway arch upper flange; and
    a conduit stabilizing bar that extends from the airway arch upper flange to the airway arch lower flange adjacent a rear portion of the airway arch, wherein:
      the respiratory interface device defines at least one channel that extends from the oxygen inlet to the oxygen outlet through at least a portion of the airway arch, the at least one channel being both partially open and partially enclosed;
      the airway arch upper flange and the airway arch lower flange define the at least one channel; and
      the conduit stabilizing bar is configured to maintain the end of the at least one conduit adjacent the air outlet within the at least one channel;
  inserting the respiratory interface device into the mouth of the patient such that the dental plate is adjacent a front of the mouth of the patient, and the airway arch extends about two-thirds back of the hard palate of the patient;
  inserting at least one tubing through the oxygen inlet and the at least one channel until an end of the at least one tubing is adjacent the oxygen outlet;
  engaging the at least one tubing with the conduit stabilizing bar to maintain the end of the at least one tubing adjacent the oxygen outlet; and
  causing at least one of:
    oxygen to flow through the at least one channel and exit the at least one channel adjacent the oxygen outlet; or
    detection of carbon dioxide exhaled by the patient through the at least one channel.

\* \* \* \* \*